(12) United States Patent
Schneider et al.

(10) Patent No.: US 8,034,929 B2
(45) Date of Patent: Oct. 11, 2011

(54) CONTINUOUS METHOD FOR PRODUCING HIGHLY METHYLOLATED MELAMINE AND ETHERIFIED MELAMINE FORMALDEHYDE RESINS

(75) Inventors: Jörg Schneider, Weinheim (DE); Günter Scherr, Ludwigshafen (DE); Rainer Erhardt, Mannheim (DE); Andreas Eichfelder, Maxdorf (DE); Martin Reif, Römerberg (DE); Stefan Hirsch, Neustadt an der Weinstraβ (DE); Hans Schupp, Worms (DE); Christel Hittinger, Mannheim (DE); Alain Robert, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 1192 days.

(21) Appl. No.: 10/586,580

(22) PCT Filed: Jan. 13, 2005

(86) PCT No.: PCT/EP2005/000259
§ 371 (c)(1),
(2), (4) Date: Jul. 19, 2006

(87) PCT Pub. No.: WO2005/068441
PCT Pub. Date: Jul. 28, 2005

(65) Prior Publication Data
US 2010/0113693 A1  May 6, 2010

(30) Foreign Application Priority Data

Jan. 19, 2004 (DE) .......... 10 2004 002 849

(51) Int. Cl.
*C07D 251/64* (2006.01)
(52) U.S. Cl. .......... 544/196; 544/200
(58) Field of Classification Search .......... 544/196, 544/200
See application file for complete search history.

(56) References Cited

U.S. PATENT DOCUMENTS

| 4,293,692 A | 10/1981 | Pai et al. |
| 4,499,125 A * | 2/1985 | Blasing et al. .......... 428/503 |

FOREIGN PATENT DOCUMENTS

| DE | 2 335 299 | 2/1974 |
| EP | 0 070 924 A2 | 2/1983 |
| EP | 0 142 628 A1 | 5/1985 |
| GB | 1030268 | 5/1966 |
| GB | 1 447 062 | 8/1976 |

OTHER PUBLICATIONS

"Kopplungseffekt Knetreaktoren fur kombinierte Prozesse mit festen und hochviskosen Produkten", Schwenk et al., *Chemietechnik*, Bd, 27, Nr. 3, Mar. 1998, pp. 70, 72 and 74.
Ullmann's Encyklopadie der technischen Chemie 4. Aufl., Bd. 7, S. pp. 403-424.

* cited by examiner

*Primary Examiner* — Venkataraman Balasubramanian
(74) *Attorney, Agent, or Firm* — Connolly Bove Lodge & Hutz LLP

(57) ABSTRACT

The invention relates to a process for preparing polymethylolated melamine and polymethylolated melamine compounds polyetherified with alkanol, wherein the methylolation reaction is carried out in a kneading reactor.

13 Claims, No Drawings

Page 1

CONTINUOUS METHOD FOR PRODUCING HIGHLY METHYLOLATED MELAMINE AND ETHERIFIED MELAMINE FORMALDEHYDE RESINS

This application is a National Stage of PCT/EP2005/000259 filed Jan. 13, 2005 which in turn claims priority from German Application 10 2004 002 849.4, filed Jan. 19, 2004.

The invention relates to a process for preparing highly methylolated melamine and highly methylolated melamine compounds polyetherified with alkanol.

The preparation of polymethylolated melamine compounds polyetherified with alkanol is common knowledge and is described, for example, in Ullmann's Enzyklopädie der technischen Chemie, 4th Edition, Volume 7, p. 403 ff.

Typically, the procedure in the preparation has several steps: initially, melamine is reacted with formaldehyde in basic aqueous medium to give polymethylolated melamine compounds including hexamethylolmelamine (HMM) and to give small proportions of corresponding oligomers which comprise 2 or 3 structural units derived from melamine and are joined together via methylene or methylene ether bridges. Alkanol is added to this reaction mixture and the pH is subsequently adjusted to from 3 to 5 and the methylol groups of the polymethylolated melamine or the corresponding oligomers are etherified.

However, this process is burdened with the following disadvantage: in the first step (methylolation), a solid (melamine) is suspended in aqueous formaldehyde solution and goes into solution as a result of the reaction. In the further course of the methylolation, precipitation of HMM in the course of the preparation of more highly methylolated melamine-formaldehyde derivatives results in an inhomogeneous, partly solidifying reaction mixture. The solids content generally increases with falling water content and falling temperature, so that corresponding reaction mixtures, when highly concentrated formaldehyde solutions are used, can no longer be fully mixed in the tank using classic stirrer units. Especially in the subsequent addition of the alkanol, further amounts of HMM precipitate out, so that the maximum stress on the stirrer is generally achieved during the addition of alkanol.

The use of water as a diluent or the use of low-concentration formaldehyde would have an advantageous effect on the stirrability and pumpability of the mixtures, but such a procedure would have an adverse effect on the etherification reaction which follows. The less water is present in the reaction mixture, the more efficiently this reaction can be performed, since this "etherification reaction" is an equilibrium reaction with water formation on the product side.

For example, DE-A 23 35 299 describes a process for preparing etherified melamine-formaldehyde resins. Example 3 discloses that HMM is prepared continuously from melamine and paraformaldehyde. The etherification is carried out in such a way that this product is introduced into a mixture of propanol and sulfuric acid. After the etherification, the product is filtered and the excess alcohol is evaporated. A disadvantage of this process is the use of the expensive paraformaldehyde which only plays a minor role on the industrial scale compared to aqueous formaldehyde solutions.

Using paraformaldehyde, the GB patent no. 1 030 268 further describes a process for preparing HMM etherified with methanol, for which the degree of etherification is on average from 4.85 to 5.15. Example 1 discloses a preparation process which, in addition to a methylolation stage, comprises two etherification stages.

It is an object of the invention to provide a simplified process for preparing polymethylolated melamine and methylolated melamine compounds polyetherified with alkanol, especially relatively highly methylolated melamine derivatives, e.g. hexamethoxymethylolmelamine. In the process, the water content of the reaction mixtures should advantageously be as low as possible. In addition, the process should advantageously be usable on the industrial scale and be implementable using inexpensive raw materials readily available on the industrial scale and simple, inexpensive effective process control.

Accordingly, a process has been found for preparing polymethylolated melamine by reacting melamine with formaldehyde, in which the methylolation reaction is carried out continuously in the presence of a catalyst in a kneading reactor.

Advantageously, melamine and formaldehyde are used in a molar ratio of from 1:4 to 1:12, preferably in a molar ratio of from 1:6 to 1:12, more preferably from 1:7 to 1:10.

Formaldehyde is advantageously used in the form of a from 35 to 95% by weight aqueous formaldehyde solution, in particular a from 40 to 70% by weight aqueous formaldehyde solution. Highly concentrated formaldehyde solutions (40-70%) may, if appropriate, also be generated from low-concentration formaldehyde solutions (20-40%) directly before the introduction into the reactor. The melamine is advantageously used in the form of a solid. If appropriate, the melamine may be mixed with the formaldehyde before introduction into the kneading reactor.

The methylolation reaction may be carried out under acid or base catalysis. These catalysts are typically metered in in accordance with the desired pH range.

Automatic/automated pH-controlled metering of the alkalis or acids preferably takes place. The catalysts used are preferably bases, advantageously alkaline earth metal or alkali metal hydroxides, in particular sodium hydroxide or potassium hydroxide in the form of their aqueous solutions, or alkali metal salts such as sodium carbonate or sodium tetraborate.

The methylolation reaction in the kneading reactor is advantageously carried out at a pH of from 6 to 12, preferably from 8 to 10. The temperature is generally from 40 to 120° C. The methylolation reaction is typically carried out for a time of from 2 to 90 minutes, preferably from 5 to 30 minutes. Highly methylolated melamine having a degree of methylolation of from 4 to 6, preferably from 4.6 to 5.8, is advantageously obtained. The degree of methylolation describes the incorporation ratio of the formaldehyde groups to the basic melamine molecule. As is well known, the degree of methylolation increases with rising reaction temperature for the same reaction time or with increasing reaction time for the same reaction temperature. Variation of these two parameters allows those skilled in the art to determine, by simple preliminary experiments, the reaction time and temperature which are required to achieve a certain degree of methylolation. The methylolated melamine is highly viscous and has a partly solidified reaction mixture.

Suitable kneading reactors are in particular single-shaft or double-shaft heatable and coolable kneading reactors, for example kneaders from List or Buss. Preference is given to kneaders having high self-cleaning of the shafts and walls, in particular those kneaders having 100% self-cleaning. Advantageously, only slight axial backmixing, if any, takes place in the kneading reactors. The performance input of the kneaders is advantageously from 0.1 to 0.8 kWh/kg.

The kneaders are, if appropriate, divided into a plurality of regions, for example into a mixing or introduction region which has metering units for liquids and solids, into a reaction region which has residence times of typically from at least two minutes up to two hours, preferably up to one hour, and into a discharge region which has discharge apparatus.

In the reaction region of the kneading reactors are advantageously disposed a plurality of heat exchangers and, for example, reflux distillation apparatuses which measure and control the temperatures. In addition, the vapor flow rate may be used to control the water content in the melamine-formaldehyde system.

The discharge from the kneading reactor may be effected, for example, via a height-adjustable overflow weir, a discharge valve, a lock feeder or via a deadspace-free single or twin screw. Preference is given to a closely intermeshing arrangement of the screws. The discharge is preferably continuous.

The methylolation reaction may be followed by an etherification reaction to give polymethylolated melamine polyetherified with alkanol. In a subsequent etherification, the polymethylolated melamine is advantageously discharged continuously from the kneading reactor.

Before or in the course of introduction of the polymethylolated melamine into the etherification medium, the methylolmelamine may, if appropriate, be subjected to a homogenization step. The homogenization and comminution may be effected with the aid of an apparatus which works by the rotor-stator principle with high frequency. The discharged methylolated melamine is preferably sent through a plurality of successive rotors turning at high frequency, and the degree of comminution is adjustable by the gap width between the rotors and the stators. Suitable apparatus are offered by companies including Ika and Ystral, for example the Dispax® (registered trademark) from Ika.

After the methylolation reaction and, if appropriate, the homogenization step, the methylolated melamine advantageously passes continuously into a reactor in which the alkanol is preferably present in excess. Advantageously, the alkanol should be present in a ratio to polymethylolated melamine of at least 5-50:1, preferably 10-30:1. The etherification reactor may consist of one or more tubular reactors, a stirred tank battery, a stirred tank or of a combination of one or more stirred tanks and one or more tubular reactors. The etherification may also be carried out in switched batch reactors, i.e. in reactors arranged in parallel to one another.

The alkanol is advantageously a $C_1$ to $C_6$ alcohol or a mixture of different $C_1$-$C_4$-alkanols; the alkanol used is preferably methanol. The carbon chain of the $C_1$-$C_6$-alkanols may, if appropriate, also comprise O-, N-, S-, Si-containing functional groups. For example, functional groups such as alkanol, amino, carbonate, urethane and/or ester groups may interrupt the carbon chain or be incorporated in a terminal position. The etherification is preferably acid-catalyzed. Useful acids include mineral acids, for example sulfuric acid or nitric acid, but also immobilized acid, for example acidic ion exchange resins. The pH is typically from 1 to 6, preferably 2-5. The reaction temperature is generally from 50° C. up to the boiling temperature of the alkanol used.

The etherification may, if appropriate, be carried out in a plurality of stages. The etherification process may lead to fully or partly etherified polymethylolated melamines. It is possible to store the partly etherified product. Between the etherification steps or during or after storage, water may be removed distillatively or using drying agents (molecular sieve, disodium sulfate) or by using membranes. The first etherification step in the tubular reactor or stirred tank may, if appropriate, also be followed by numerous further etherification steps in different reactors (stirred tanks or tubular reactors). After the last, if appropriate also after preceding etherification steps, may follow continuous distillations using suitable evaporators (for example, falling-film evaporators, thin-film evaporators, tanks with external heat exchangers, and the like). Using a stirred tank, only partly etherified melamine compounds are advantageously obtained in a first step. If required, further etherification steps may follow and are advantageously carried out in a tubular reactor.

The etherified methylolated melamine may, if required, be filtered and/or concentrated, and/or the viscosity of the product may be adjusted by adding solvents (for example water, $C_1$-$C_6$-alkanols or aliphatic or aromatic hydrocarbon compounds).

The etherified and methylolated melamine obtained in this way typically has a viscosity of from 1500 to 80 000 mPas, preferably 3000-10 000 mPas. The melamine: etherified formaldehyde groups ratio is, on average, advantageously between 1:4 and 1:6, preferably between 1:4.7 and 1:5.8. The monomer content is generally from 20 to 98%, preferably from 30 to 70%. The main components are typically mono- and dinuclear, highly methylolated and etherified derivatives, in particular hexamethoxy-methylolmelamine.

The etherified and methylolated melamine compounds prepared by this process are suitable in particular as crosslinking systems in coating compositions such as varnishes.

One advantage of the process according to the invention is that inexpensive raw materials, i.e. highly concentrated aqueous formaldehyde solution, may be used which, in a methylolation reaction in a stirred tank, would lead to partly solidified methylolated melamine compounds which cannot be handled; another is that the use of highly concentrated formaldehyde allows the water which is troublesome in the etherification reaction to be minimized.

In the inventive process for preparing etherified methylolated melamines, it is possible to dispense with isolation of the methylolated melamine. In addition, the reaction volume is reduced in comparison to the batch process. Moreover, uniform product quality can be readily controlled and it is possible to attain high degrees of etherification.

EXAMPLE

A 250 ml kneading reactor with heatable kneading tools and jacket was charged with a feed of 394.9 g/h of a 60 percent by weight aqueous formaldehyde solution (admixed with 0.73 g of borax and adjusted to a pH of 8.5-8.8 using 30 percent sodium hydroxide solution). The attached solids metering apparatus was used to meter in 99.6 g/h of solid melamine in the mixing region of the kneader. Downstream of the mixing region was a heating zone in which the mixture was preheated to approx. 60° C. In the subsequent reaction stage which was equipped with a reflux condenser, cooling and establishment of a suitable reflux ratio kept the temperature at approx. 100° C. After an average residence time of approx. 15 min, the reaction mixture was introduced, by means of a discharge screw out of the reactor, directly into a continuous tank system. This tank was charged at 60° C. with a feed of 252.8 l of methanol (acidified with 3.5 ml of 30% nitric acid). After an average residence time of approx. 30 min (minimum residence time 15 min), the mixture was introduced into a downstream tubular reactor which was charged with a feed of 800 ml/h of methanol (pH 3.8, temperature 60° C.). After an average residence time of 60 min, the mixture was conducted directly to two falling-film evaporators connected in series ($p_1$ 1 bar, $p_2$ 100 mbar). After filtration, the product was analyzed by HPLC: it comprised 20 area percent (HPLC) of hexamethoxymethylolmelamine, and also further highly methylolated/etherified components. The total concentration of the monomers was 60 area percent (HPLC-GPC).

What is claimed is:

1. A process for preparing polymethylolated melamine by reacting melamine and formaldehyde, which comprises carrying out the methylolation reaction continuously in the presence of a catalyst in a kneading reactor and using melamine and formaldehyde in a molar ratio of from 1:4 to 1:10, wherein the formaldehyde is used in the form of a from 35 to 95% by weight aqueous formaldehyde solution, wherein the polymethylolated melamine has a degree of methylolation of from 4.6 to 5.8, and wherein the methylolation reaction is carried out at a pH is from 8 to 10.

2. The process according to claim 1, wherein the methylolation reaction is carried out at a temperature of from 40 to 120° C.

3. The process according to claim 1, wherein the methylolation reaction is carried out for from 2 to 90 minutes.

4. The process according to claim 1, wherein the kneading reactor used is a single-shaft or double-shaft heatable and coolable kneader.

5. A process for preparing polymethylolated melamine polyetherified with alkanols, which comprises
carrying out the methylolation reaction according to claim 1,
continually discharging methylolated melamine from the kneading reactor and
continuously introducing the discharged methylolated melamine into a reactor and reacting with an alcohol which is present in excess.

6. The process according to claim 5, wherein the continuous discharge of step (ii) is effected by means of an overflow weir, a discharge valve, a lock feeder or a single or twin screw.

7. The process according to claim 5, wherein the etherification of step (iii) is carried out continuously.

8. The process according to claim 5, wherein the etherification of step (iii) is carried out in an apparatus selected from the group consisting of switched batch reactors, a tank battery, one or more tubular reactors and a tank having downstream reactor, and leads to partly or fully etherified, polymethylolated melamine.

9. The process according to claim 8, wherein the etherification of step (iii) leads via several stages with intermediate distillation to partly or fully etherified, polymethylolated melamine.

10. The process according to claim 5, wherein the methylolated melamine discharged from the kneading reactor is subjected to a homogenization process before introduction into the etherification reactor.

11. The process according to claim 2, wherein the methylolation reaction is carried out for from 2 to 90 minutes.

12. The process according to claim 2, wherein the kneading reactor used is a single-shaft or double-shaft heatable and coolable kneader.

13. The process according to claim 3, wherein the kneading reactor used is a single-shaft or double-shaft heatable and coolable kneader.

\* \* \* \* \*